(12) United States Patent
Vinogradov et al.

(10) Patent No.: US 9,170,239 B2
(45) Date of Patent: Oct. 27, 2015

(54) MAGNETOSTRICTIVE SENSOR HAVING CRIMPED MAGNETOSTRICTIVE STRIP FOR HIGH TEMPERATURE OPERATION

(71) Applicant: Southwest Research Institute, San Antonio, TX (US)

(72) Inventors: Sergey A. Vinogradov, San Antonio, TX (US); Hegeon Kwun, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 234 days.

(21) Appl. No.: 13/792,090

(22) Filed: Mar. 10, 2013

(65) Prior Publication Data

US 2014/0253110 A1 Sep. 11, 2014

(51) Int. Cl.
*G01N 27/82* (2006.01)
*B32B 7/00* (2006.01)
*G01N 29/24* (2006.01)

(52) U.S. Cl.
CPC .... *G01N 29/2412* (2013.01); *G01N 2291/0234* (2013.01); *G01N 2291/0289* (2013.01); *G01N 2291/045* (2013.01); *G01N 2291/2634* (2013.01)

(58) Field of Classification Search
CPC .............................. G01N 27/82; G01N 27/9046
USPC .................. 324/20, 239, 240, 754.06, 754.19; 73/643; 204/404, 400
See application file for complete search history.

(56) References Cited

U.S. PATENT DOCUMENTS

| | | | | |
|---|---|---|---|---|
| 5,854,557 A * | 12/1998 | Tiefnig | ................... | G01N 17/00 204/404 |
| 6,396,262 B2 | 5/2002 | Light et al. | | |
| 6,917,196 B2 | 7/2005 | Kwun et al. | | |
| 7,573,261 B1 * | 8/2009 | Vinogradov | ........... | G01N 27/82 324/240 |
| 7,821,258 B2 | 10/2010 | Vinogradov | | |
| 2009/0142570 A1 * | 6/2009 | Boylan | ..................... | B32B 5/26 428/221 |
| 2010/0052669 A1 * | 3/2010 | Kwun | ................... | G01N 29/043 324/240 |

* cited by examiner

*Primary Examiner* — Patrick Assouad
*Assistant Examiner* — Taqi Nasir
(74) *Attorney, Agent, or Firm* — Livingston Law Firm; Ann C. Livingston

(57) ABSTRACT

A sensor for use in magnetostrictive testing of a structure. The sensor has a thin ferromagnetic strip with a series of parallel crimps across its width. A first wire coil is wrapped around the width of the strip and along its entire length, such that portions of wire that cross the bottom surface of the strip are located inside the crimps, and portions of wire that are wrapped across the top surface of the strip are between the crimps. The sensor further has a second coil wrapped around the length of the strip, or for pipeline applications, around the pipeline.

18 Claims, 7 Drawing Sheets

MAGNETOSTRICTIVE SENSOR HAVING CRIMPED MAGNETOSTRICTIVE STRIP FOR HIGH TEMPERATURE OPERATION

TECHNICAL FIELD OF THE INVENTION

This invention relates to nondestructive testing using guided wave testing (GWT) and magnetostrictive sensor (MsS) technology, and more particularly, to a sensor used for magnetostrictive testing.

BACKGROUND OF THE INVENTION

Many processing plants, such as refineries, chemical plants, and electric power generation plants, use networks of pipelines. Failure of these pipelines can cause major disruption of plant operation and an unscheduled outage. To ensure safe operation of such plants, there is a need for on-line non destructive testing methods to inspect and monitor pipelines.

One effective method for inspecting and monitoring a long length of pipelines is guided wave testing (GWT) using magnetostrictive sensor (MsS) technology. A common implementation of this method uses primarily torsional waves (T-waves) that are generated in a thin ferromagnetic strip placed around and coupled to the pipe under test. If the generated waves are coupled to the pipe, the waves propagate along the pipe and are partially reflected by geometric irregularities present in the pipeline, such as welds or corrosion defects.

The reflected signals are then detected in a pulse-echo mode. From the arrival time of the reflected signal and the signal amplitude, the axial location of the irregularity and its severity are determined. In above-ground pipelines, this method can detect 2 to 3% defects over 500 feet from an MsS sensor location. The % refers to the defect's cross-sectional area relative to the total cross section of the pipe wall.

Magnetostrictive testing, although especially useful for testing pipelines, is not limited that type of testing. Magnetostrictive testing has been adapted for testing of structures of other shapes, and in general, can be used to test for defects in any shape, even to plate structures.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

As described in the Background, common implementations of magnetostrictive sensor (MsS) testing use primarily torsional waves (T-waves) that are generated in a thin ferromagnetic strip placed on and coupled to the material being tested. To produce T-waves, MsS testing requires a perpendicular relationship between DC bias magnetic fields needed for MsS sensor operation and AC magnetic fields applied to generate waves.

In the examples of this description, the MsS method is discussed in terms of non destructive testing (inspection and/or monitoring) of cylindrical structures such as pipelines. However, the sensor described herein and the methods of using it are not limited to pipelines, and can be used to test any shape of structure. The structure can be "tubular", meaning any long hollow structure, with cross sectional geometry that can be circular, rectangular or other, and can be closed or open channeled. Or, as another example, the structure can be planar.

Figure 1:
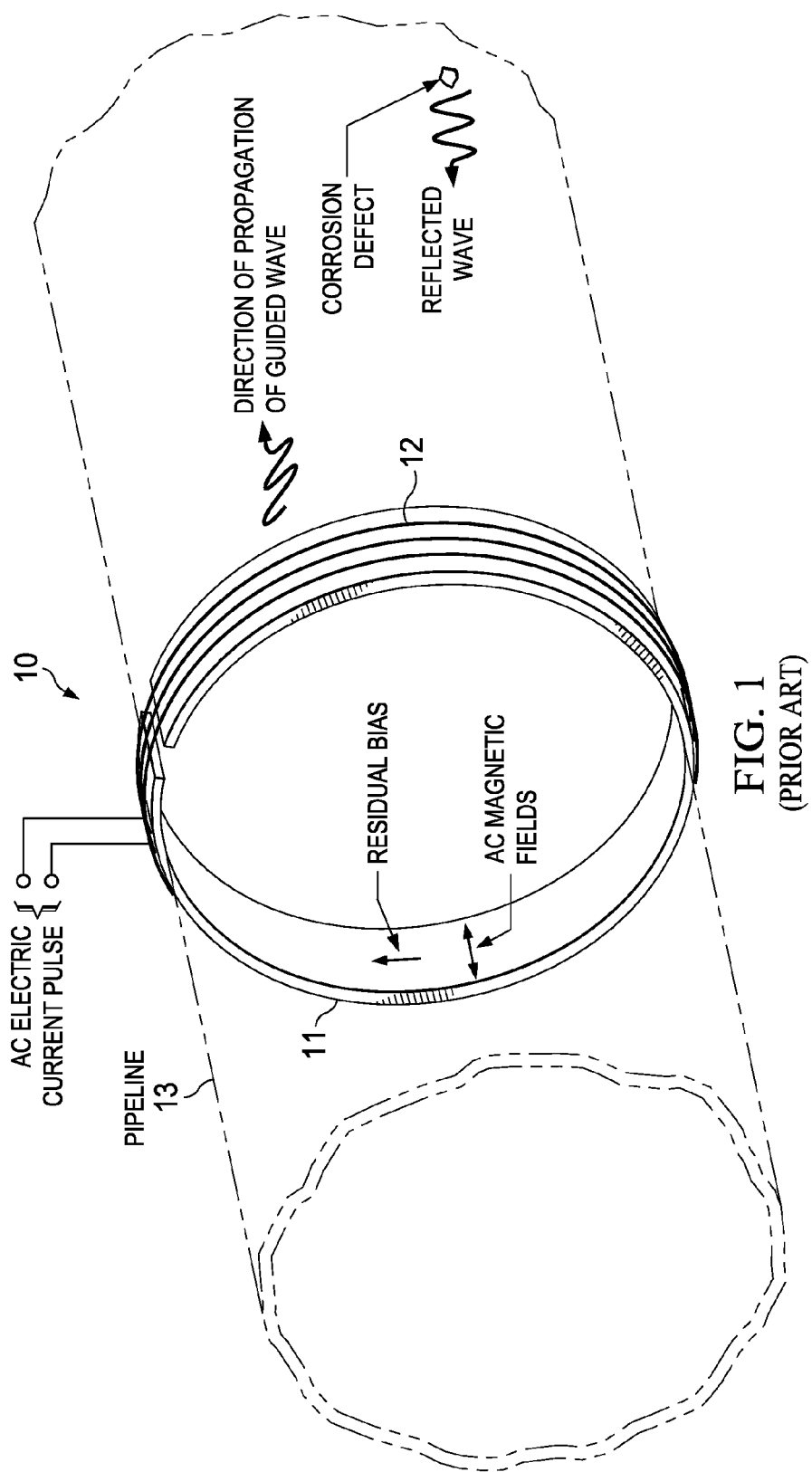
FIG. 1 illustrates one of various known configurations for implementing MsS testing of pipelines.

FIG. 1 illustrates one of various known MsS sensor configurations for testing pipelines, and here serves as an example for the principle of operation of MsS testing. Here, the MsS sensor 10 comprises a ferromagnetic strip 11 and an MsS coil 12. The MsS sensor 10 is used for T-wave generation and detection using strip 11 and MsS coil 12, and is suitable for inspection as well as long term monitoring.

DC bias fields are established in the circumferential direction of pipeline 13 by inducing residual magnetization along the length of ferromagnetic strip 11 placed around the pipe. AC magnetic fields are applied in the lengthwise direction of pipeline 13 by applying an AC voltage to coil 12, which is placed over strip 11 and encircles the circumference of the pipeline.

The T-waves generated in strip 11 are coupled to pipe 13 and propagate along the length of the pipe. The coupling may be achieved by various means. Examples of suitable coupling methods are bonding the strip with adhesive material (such as epoxy), or using a viscous coupling medium (such as shear wave couplant or honey), mechanically pressing the strip against the pipe with a mechanical tool (such as bladder or clamp), and soldering or spot welding.

When reflected waves from irregularities in the pipeline (such as corrosion defects, notches, cuts, cracks or welds) return back to the location of strip 11, the waves are coupled to strip 11. This induces voltage signals in MsS coil 12 through inverse magnetostrictive effects and are detected by MsS instrument electronics (not shown).

As stated above, the same concepts can be applied to testing structures other than pipelines. Also, because the magnetostrictive vibration is produced inside ferromagnetic strip 11, it can be transferred to (and from) a structure of any material via mechanical coupling.

MsS sensor 10 and other known MsS sensors, as well as various MsS techniques, are described in the following patents, each incorporated herein by reference: U.S. Pat. No. 6,396,262 to Light, et al.; U.S. Pat. No. 6,917,196 to Kwun, et al.; U.S. Pat. No. 7,573,261 to Vinogradov; and U.S. Pat. No. 7,821,258 to Vinogradov.

Figure 2:
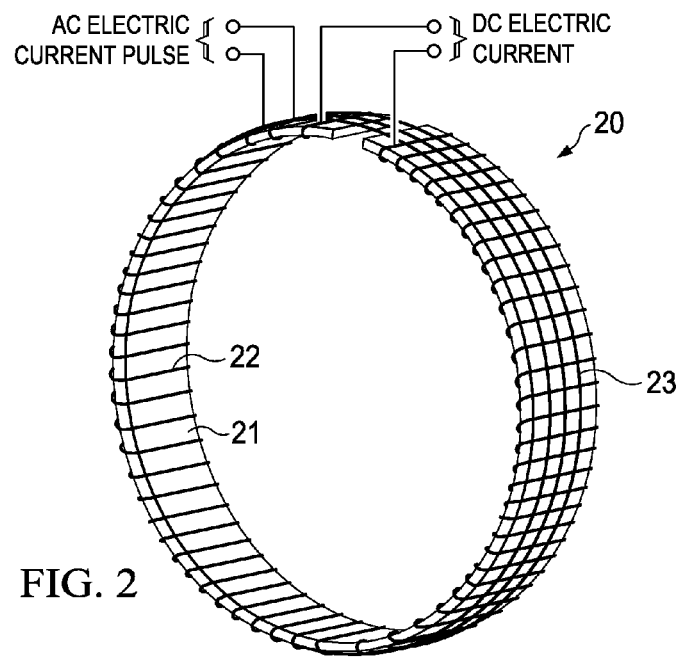
FIG. 2 illustrates an alternative MsS sensor 20, which uses two coils for providing the DC and the AC magnetic fields in the circumferential and the lengthwise directions of pipe, respectively.

FIG. 2 illustrates an alternative MsS sensor 20, which uses two coils for providing the DC and the AC magnetic fields in the circumferential and the lengthwise directions of pipe. A first coil 22 is wound around the width (short axis) of ferromagnetic strip 21. A second coil 23 is placed over strip 21, wound along its length (long axis) and around the outer circumference of the pipe. As explained below, strip 21 has a unique crimped design for holding the wrapped wires of coil 22.

As in FIG. 1, ferromagnetic strip 21 is wrapped around the pipe (not shown). Strip 21 almost encircles the pipe except for a small gap between its ends. An example of a suitable material for strip 11 is a FeCo alloy.

Thus, the MsS sensor 20 has two coils 22 and 23 in addition to strip 21. One of the coils is used as the "electromagnetic coil" for application of the DC bias magnetic fields. The other coil is used as the "MsS coil" for application of AC magnetic fields and guided wave generation and detection. As explained below, the roles of coils 22 and 23 may be alternated. That is, the MsS method may be implemented with either coil acting in either capacity. In either case, the DC bias magnetic fields and the applied AC magnetic fields are perpendicular from each other and both are located in the plane of the strip 21 to produce T-waves in the strip.

Figure 3:
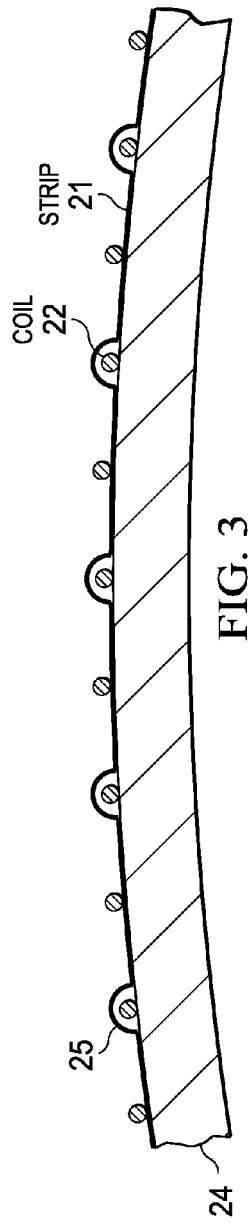
FIG. 3 is a side view of a portion of the coil and strip of FIG. 2.
Figure 4:
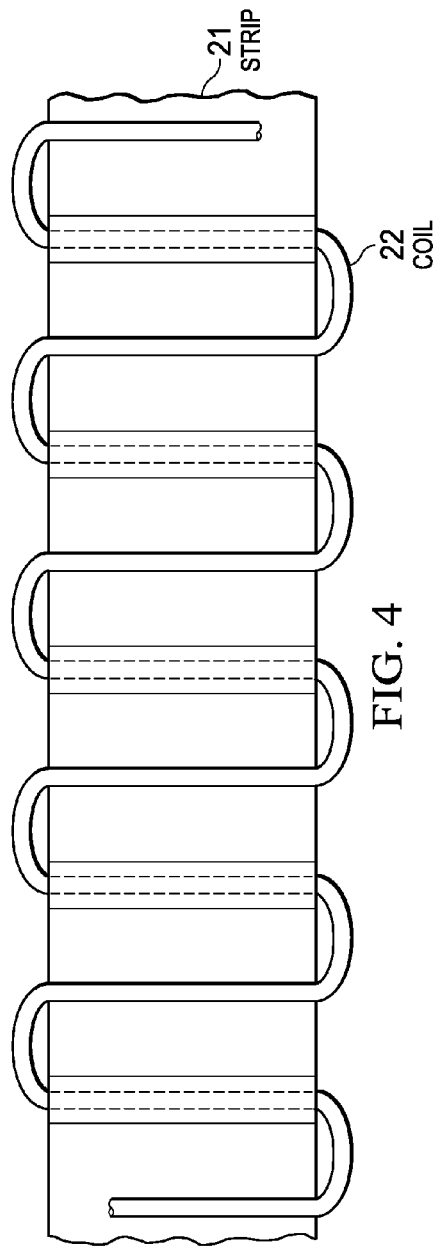
FIG. 4 is a plan view of a portion of the coil and strip of FIG. 2.

FIGS. 3 and 4 illustrate a portion of strip 21 and coil 22 of FIG. 2 in further detail. FIG. 3 is a side view also showing a portion of pipe 24. FIG. 4 is a plan view from the outside of pipe 24.

To minimize coupling problems and potential damage to coil 22 wound around strip 21, strip 21 has crimps 25 at regular intervals. Crimps 25 are raised portions of the strip 21 across its width. Where the "bottom" surface of strip 21 is the surface to be placed against the pipeline, the crimps 25 are raised toward the top surface of strip 21. Typically, crimps 25 are evenly spaced (at regular intervals) and uniform in size.

Coil 22 is wound through the crimped locations. In the example of FIGS. 3 and 4, a single wire of coil 22 passes under and through each crimp 25. In other embodiments, coil 22 can have multiple turns routed though and under each crimp.

Crimps 25 may be of various geometries and spacing. The crimps 25 of FIG. 3 are rounded "bumps", but other geometries are possible, such as rectangular or triangular "bumps". The crimps 25 may be formed by plastic or elastic deformation of the strip 21. In general, each crimp 25 is sufficiently large to allow a single wire of coil 22 to pass through it. The passage of the wire through each crimp 25 may be a relatively close fit, that is, the inner geometry of each crimp 25 need only be slightly larger than the outer diameter of the wire.

The crimped configuration of strip 21 allows direct physical contact between strip 21 and the outer diameter surface of the pipe 24 for coupling of guided waves between the two. In other words, because the portions of coil 22 that are on the underside of strip 21 are inside crimps 25, they do not "lift" strip 21 away from the surface being tested.

Figure 5:
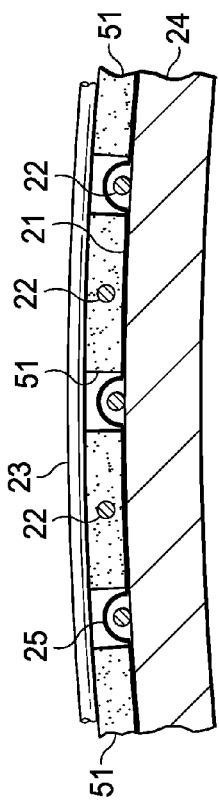
FIG. 5 further illustrates the arrangement of the two coils and details of padding between the strip and the outer coil of the sensor of FIGS. 2-4.

FIG. 5 further illustrates the arrangement of the two coils 22 and 23 and details of the area between the strip 21 and the outer coil 23. A cross-sectional portion of sensor 20 is shown; in practice, for testing a pipeline, the entire sensor 20 would be operable to surround the outer diameter of a pipeline as in FIG. 2.

Coil 22 is wrapped around the width of strip 21, typically along its entire length. The portions of coil 22 that are wrapped across the bottom surface of strip 21 are located inside crimps 25. The portions of coil 22 that are wrapped across the top surface of strip 21 are between crimps 25.

In operation, the guided waves generated in strip 21 are dry coupled to the pipe 24. This dry coupling may be achieved in various ways, such as by pressing the strip 21 with about 30 to 40 psi of pressure and/or by using a thin layer of high temperature ceramic epoxy between the strip 21 and the pipe 24. The needed pressure may be supplied by using a mechanical clamp or mechanical bladder that is placed over and around the outer coil 23.

To preserve the crimps 25 of the strip 21 under any pressure that may be caused by mechanical coupling of strip 21 to the pipe 24, an optional non-conducting padding layer 51 may be placed in the space between strip 21 and outer coil 23 and between crimps 25. Padding layer 51 is made from a material that transmits pressure to prevent crimps 25 from being deformed under external pressure during coupling. Examples of suitable material for padding layer 51 are high temperature fiberglass or carbon fiber woven tape.

The padding layer 51 is placed along the length of the strip 21. It at least fills the space between the crimps 25, and may also cover the crimps 25.

In FIG. 5, the portions of coil 22 that are wrapped across the top surface of strip 21 are embedded in the padding layer 25. In other embodiments, the padding layer 25 may be over or under these portions of coil 22. If no padding is used, some other means is used to electrically separate coils 22 and 23.

Because of the above-described features, sensor 20 is especially suitable for MsS guided wave testing (both inspection and long-term monitoring) of pipelines in temperatures over 500° C. (or 932° F.). The FeCo alloy used for strip 21 has a high Curie temperature (1720° F. or 938° C.) and therefore is suitable for high temperature use. The coils 22 and 23 are made of high temperature wires that are rated to operate in the targeted temperature range of MsS testing.

Furthermore, sensor 20 can withstand mechanical coupling pressures to allow good coupling between the strip 21 without use of coupling adhesives and the like that degrade in high temperature. Also, the strip 21 of sensor 20 can be spot welded to the pipe in areas between the crimps 25. Coil 22 is well protected to maintain the required DC bias magnetic fields under high temperature conditions.

In an alternative embodiment of sensor 20, suggested but not explicitly shown, coil 22 is segmented. In other words, instead of a continuous coil along the length of strip 21, there are two or more coils in segments. The segmented coils may then be used as individual MsS coils for more detailed examination of the pipeline around its circumference.

Figure 6:
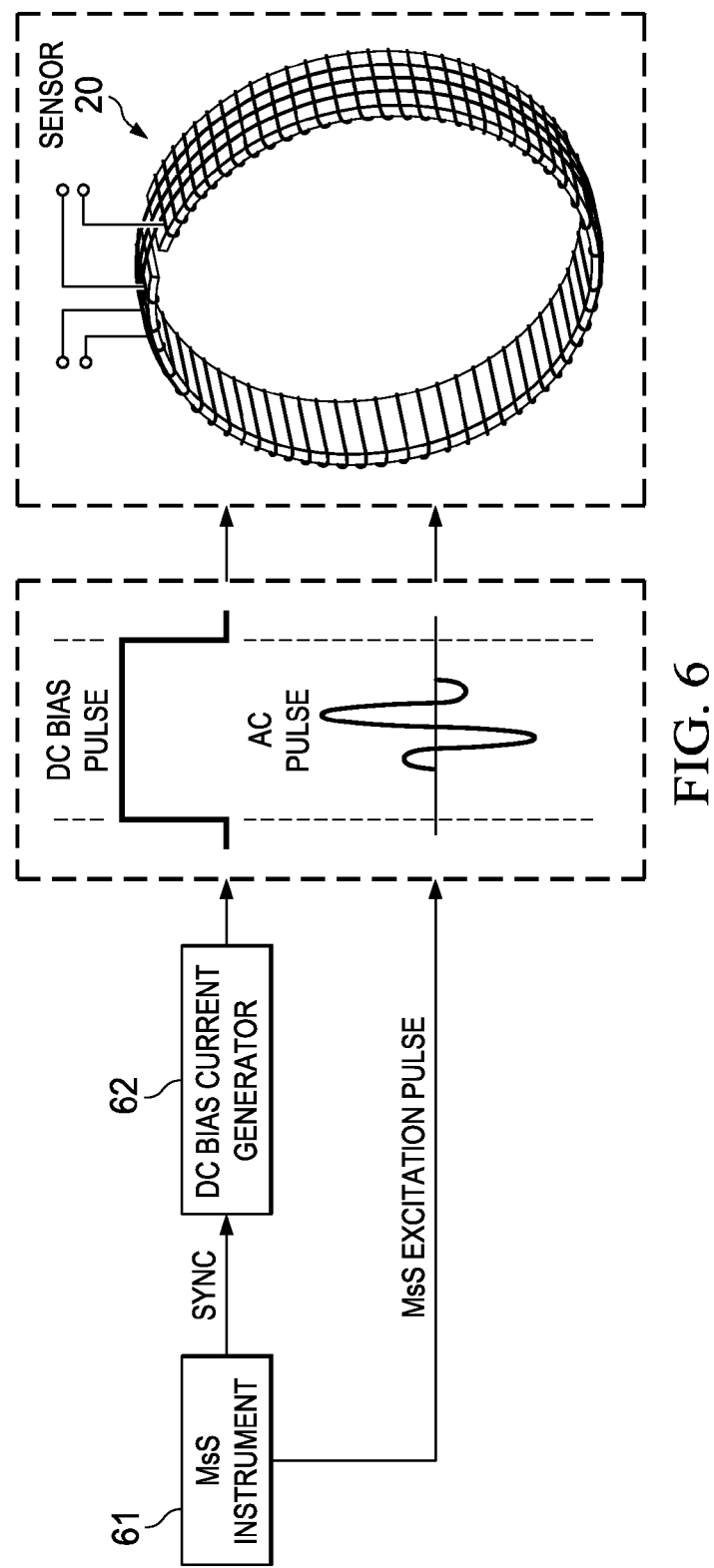
FIG. 6 is a block diagram of electronic instruments system for implementing MsS testing with the sensor of FIGS. 2-5.

FIG. 6 is a block diagram of electronic instrumentation for implementing the MsS method with the sensor 20 of FIGS. 2-5. As stated above, coils 22 and 23 can serve either role as MsS coil or electromagnetic bias coil. Thus, coil 22 has electrical leads for connection to either a DC bias pulse or an AC pulse. Coil 23 has electrical leads for connection to the pulse not being connected to coil 22.

An MsS unit 61 applies an AC current pulse to the MsS coil 22 (or 23). MsS unit 61 also detects the voltage signals induced in the MsS coil 22 (or 23) by guided waves reflected back from irregularities. A DC bias current generator 62 applies a pulse of DC bias current to the electromagnetic coil 22 (or 23) during the transmission of guided waves. The reception of the guided wave pulse is aided by using the residual magnetic field in the strip that is always perpendicular to the time-varying magnetic field.

The DC bias current generator 62 is synchronized with the MsS unit 61 so that the DC bias current pulse is "turned on" during the application of the AC current pulse to the MsS coil 23 and is "turned off" afterwards. In this operating mode, the reception of the guided wave is aided by using the residual magnetic field. The duration of the DC bias current pulse is controlled to be at least 1.5 times longer than the duration of the AC current pulse.

In an alternative operating mode, a DC current pulse can stay "on" for a longer period of time to support not only the transmission but also the reception of the guided wave signal. In this case, the time "on" can be as long as 1000 ms. The pulse repetition rate in this mode should be essentially slower and have about 10 times longer a period than the duration of the DC pulse. This keeps the duty cycle of the pulser 62 at a 10% level. This mode of pulse generation and reception is useful at temperatures between 700-900 C, at which sensor 20 can operate as a magnetostrictive sensor but cannot support a residual bias field due to a lower coercive force caused by recrystallization mechanisms at temperatures higher than 720 C.

Figure 8:
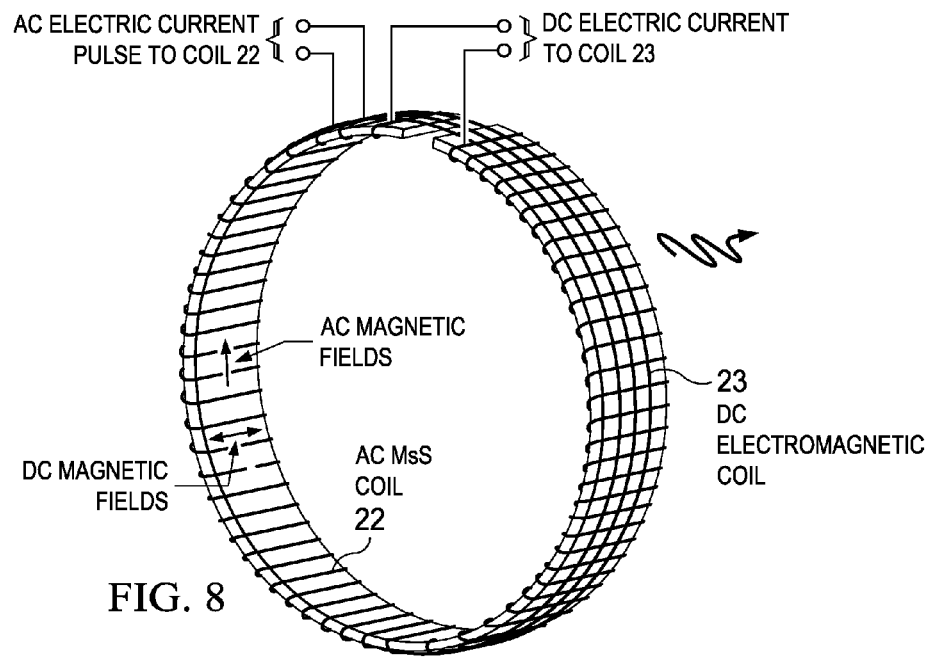
FIGS. 7 and 8 illustrate how the functions of the two sensor coils may be reversed.
Figure 7:
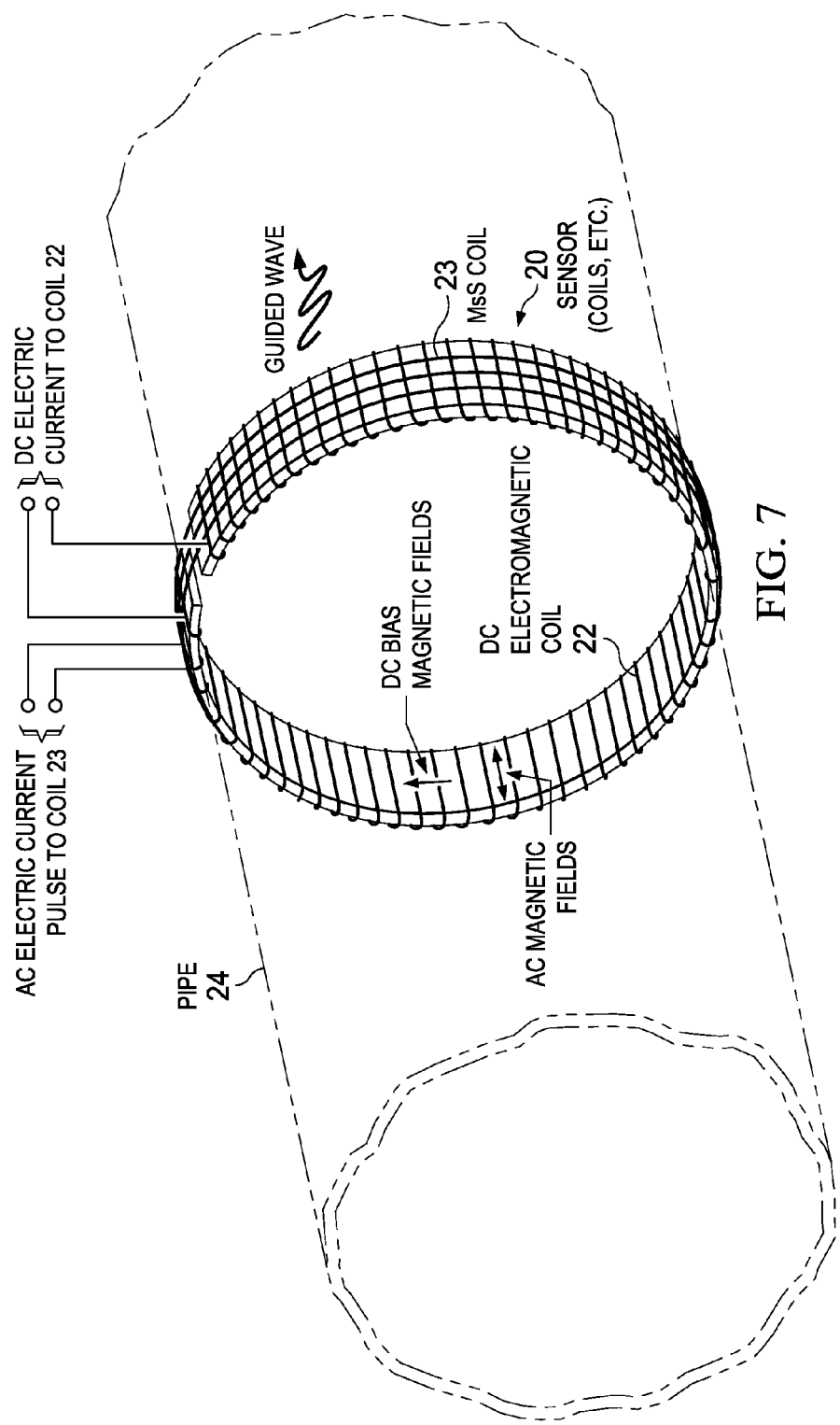

FIGS. 7 and 8 illustrate how the roles of coils 22 and 23 may be reversed. In FIG. 7, coil 22 is used as the DC electromagnetic coil and the outer coil 23 is used as the MsS coil. The DC bias is circumferential and the AC magnetic fields are applied in the direction lengthwise to the pipe (indicated with dashed lines). In FIG. 8, coil 22 is used as the MsS coil and the outer coil 23 is used as the DC electromagnetic coil. The DC bias is lengthwise and the AC magnetic fields are applied are circumferential to the pipe. Either configuration may be used to implement MsS methods for detecting pipeline defects.

Figure 9:
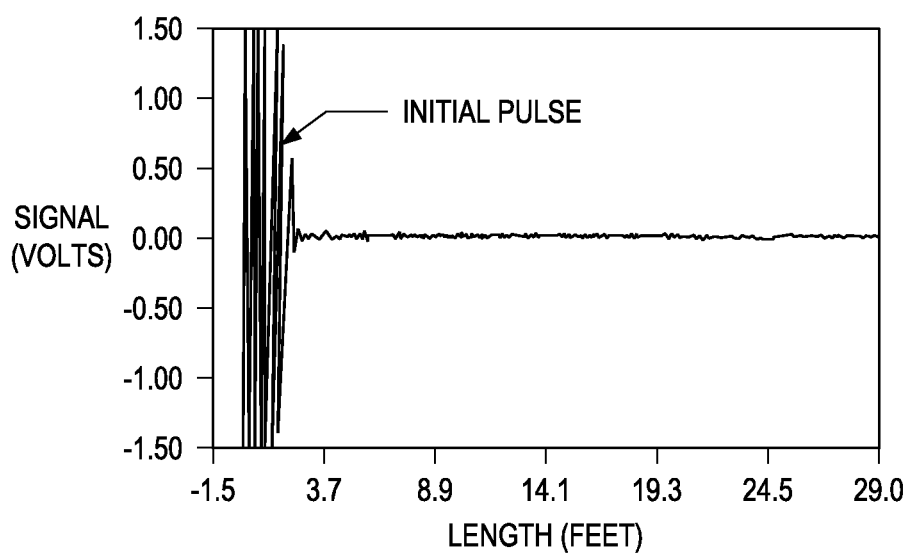
FIGS. 9 and 10 are plots of T-wave data from a sample pipeline, using the sensor in ambient temperature.
Figure 10:
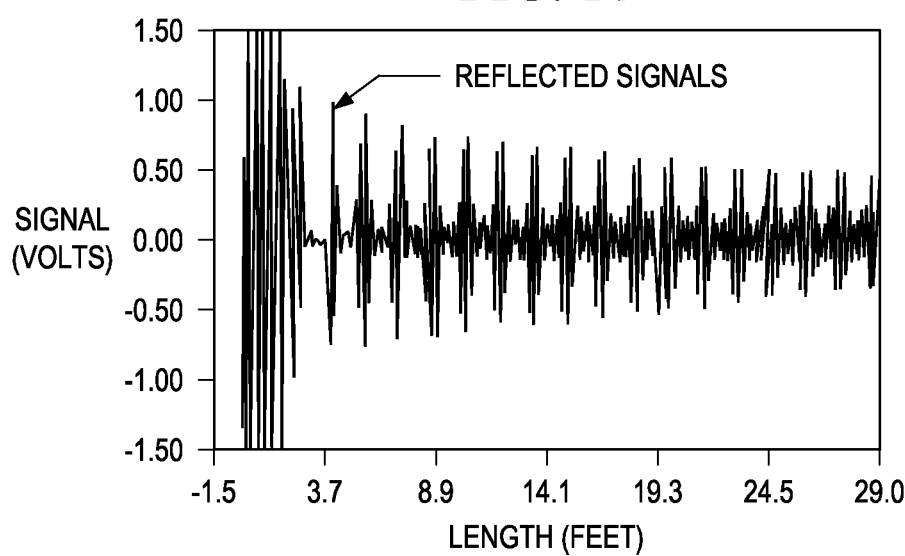

FIGS. 9 and 10 are plots of T-wave data from a 3.5 ft long sample pipeline, using sensor 20 in ambient temperature. In FIG. 9, the DC bias current generator 62 was turned off. In FIG. 10, the DC bias current generator 62 was turned on.

In the example of FIGS. 9 and 10, the coil 22 wound around the strip 21 was used as the DC electromagnetic coil and the outer coil 23 was used as the MsS coil. As shown in FIG. 9, when the DC bias current generator was turned off, there were no bias magnetic fields and consequently there were no detectable signals. As shown in FIG. 10, when the DC bias current generator was turned on, sensor 20 produced large signals that were reflected from the far end of the pipe while propagating back and forth between the two ends of the pipe sample.

Figure 11:
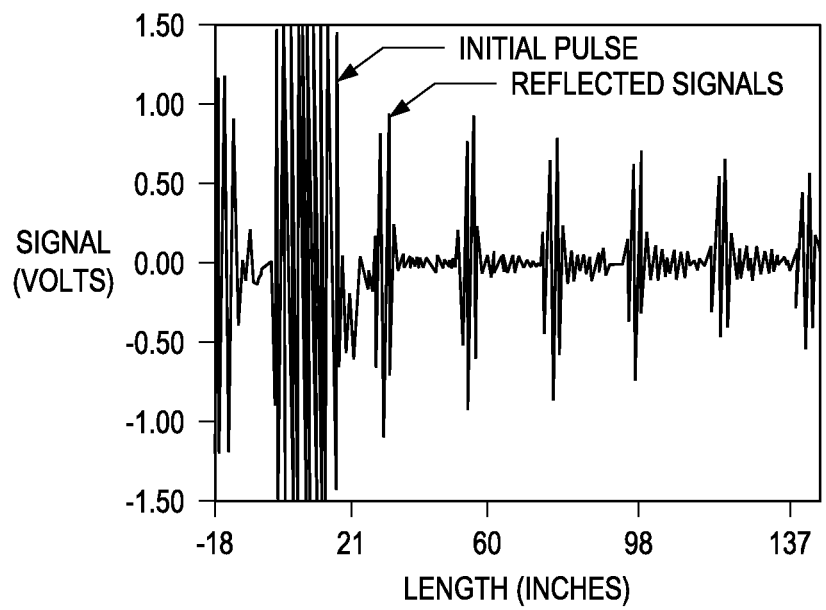
FIGS. 11 and 12 are plots of T-wave data from a pipe sample obtained using the sensor at 20° C. and 700° C., respectively.
Figure 12:
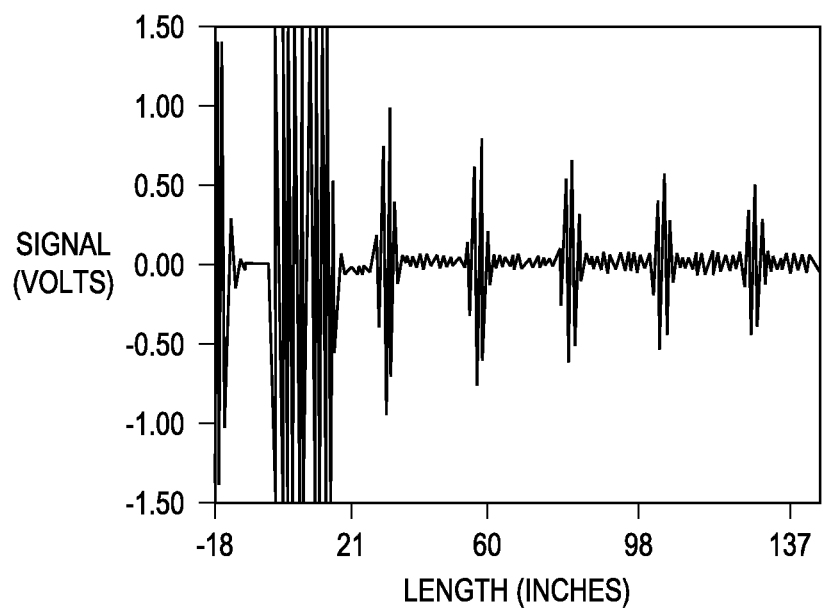

FIGS. 11 and 12 are plots of T-wave data from a pipe sample obtained using sensor 20 at 20° C. and 700° C., respectively. These plots represent laboratory data obtained from a 25 inch long pipe sample placed in a high temperature oven.

The data of FIGS. 11 and 12 demonstrate the applicability of sensor 20 and an MsS method of using sensor 20 for guided wave testing of high temperature pipelines. Sensor 20 was installed at one end of the pipe, using ceramic epoxy as coupling medium and a mechanical hose clamp as the device holder. In this test, the coil 22 wound around the strip 21 was used as the DC electromagnetic coil and the outer coil 23 was used as the MsS coil.

The large signals in the data plots are those reflected from the far end of the sample while the guided waves were propagating back and forth between the two ends of the sample. As shown, sensor 20 performed well at the elevated temperature. The end reflected signals in FIG. 12 are separated more than those in FIG. 11 because of a slower wave velocity at high temperatures. Sensor 20 can be easily adapted for non destructive testing of structures other than pipelines. As stated above, the structure may be of any material, provided that appropriate mechanical coupling between sensor 20 and the surface under test is achieved.

For testing tubular structures that are not exactly circular in cross section, sensor 20 will generally conform to the outer diameter, rather than having the circular geometry of FIG. 2. Typically, for testing tubular structures, strip 21 is sufficiently flexible to be wrapped around the outer cross sectional surface of the structure being tested, e.g., the outer circumference of a cylindrical pipeline or other analogous outer cross sectional surface.

For testing planar structures, sensor 20 has a flat geometry so that sensor 20 may be laid flat on the surface of the structure. Strip 21 and coil 22 are flat. The outer coil 23 is wrapped over the padding or other insulation, around the lengthwise dimension of strip 21. Strip 21 may have a "u" channel shape, with coil 23 wrapped within the channel, and with the open channel facing the surface being tested.

An additional advantage of crimps 25 is that they serve as a stress relief mechanism for areas of strip 21 that are transmitting and receiving magnetostrictive signals. With crimps 25, strip 21 is less likely to undergo unwanted changes in its magnetic properties resulting from stress-strain applied to it as a result of thermal cycling.

What is claimed is:

1. A sensor system for use in magnetostrictive testing of a structure, by transmitting a guided wave and receiving a reflected signal, comprising:
   a thin strip made from ferromagnetic material, the strip having a bottom surface for placement against the structure and a top surface;
   wherein the strip has a series of crimps across its width, each crimp being a raised portion of the strip, raised toward or above the top surface of the strip, such that the strip is non planar on both surfaces;
   a first wire coil wrapped around the width of the strip and along its entire length;
   wherein wires of the first coil that are wrapped across the bottom surface of the strip are located inside the crimps, and wires of the first coil that are wrapped across the top surface of the strip are between the crimps;
   a second wire coil wrapped around the length of the strip;
   wherein the crimps are raised sufficiently from the structure when the strip is coupled to the structure, such that wires of the first coil are contained within the crimps and do not lift the bottom surface of the strip from the structure.
   an AC pulse generator for applying AC pulses to either the first coil or the second coil; and
   a DC bias current generator for applying a DC bias current to whichever of the first coil or the second coil does not receive the AC pulse;
   wherein the DC bias current generator is further operable to apply the DC bias current during each AC pulse and for a period of time corresponding to both transmission of the guided wave and reception of the reflected signal and having a duty cycle of 10% or less.

2. The sensor system of claim 1, wherein the structure is a tubular structure, and the thin strip is sufficiently flexible to be wrapped around the outer cross sectional surface of the structure.

3. The sensor system of claim 1, further comprising a padding layer placed along the length of the strip, at least between the crimps.

4. The sensor system of claim 1, wherein a single wire of the first coil is placed under each crimp.

5. The sensor system of claim 1, wherein the padding layer is operable to prevent deformation of the crimps when pressure is applied to the sensor to mechanically couple the sensor to the surface of the structure.

6. The sensor system of claim 1, wherein the first coil or the second coil or both are segmented.

7. A sensor system for use in magnetostrictive testing of a tubular structure, by transmitting a guided wave and receiving a reflected signal from a defect, comprising:

a thin strip made from ferromagnetic material, the strip having a bottom surface for placement against the structure and a top surface;

wherein the strip has a series of crimps across its width, each crimp being a raised portion of the strip, raised toward the top surface of the strip, such that the strip is non planar on both surfaces;

wherein the strip is sufficiently flexible such that it may be pressed around the outer cross sectional surface of the tubular structure;

a first wire coil wrapped around the width of the strip and along its entire length;

wherein wires of the first coil that are wrapped across the bottom surface of the strip are located inside the crimps, and wires of the first coil that are wrapped across the top surface of the strip are between the crimps;

a second wire coil wrapped around the circumference of the tubular structure wherein the crimps are raised sufficiently from the tubular structure when the strip is coupled to the tubular structure, such that wires of the first coil are contained within the crimps and do not lift the bottom surface of the strip from the tubular structure.

8. The sensor system of claim 7, further comprising a padding layer placed along the length of the strip, at least between the crimps.

9. The sensor system of claim 8, wherein the padding layer may be over, under or embed the portions of the coil that are wrapped across the top surface of the strip.

10. The sensor system of claim 7, wherein a single wire of the first coil is placed under each crimp.

11. The sensor system of claim 8, wherein the padding layer is operable to prevent deformation of the crimps when pressure is applied to the sensor to mechanically couple the sensor to the surface of the structure.

12. The sensor system of claim 7, wherein the first coil or the second coil or both are segmented.

13. A method of using a magnetostrictive sensor for testing of a structure, by transmitting a guided wave and receiving a reflected signal from a defect in the structure, comprising:

placing a magnetostrictive sensor against the surface of the structure, the sensor comprising a thin strip made from ferromagnetic material, the strip having a bottom surface for placement against the structure and a top surface;

wherein the strip has a series of crimps across its width, each crimp being a raised portion of the strip, raised toward or above the top surface of the strip, such that the strip is non planar on both surfaces;

a first wire coil wrapped around the width of the strip and along its entire length;

wherein portions of the first coil that are wrapped across the bottom surface of the strip are located inside the crimps, and portions of the first coil that are wrapped across the top surface of the strip are between the crimps; and a second wire coil wrapped around the length of the strip or around the structure;

wherein the crimps are raised sufficiently from the structure when the strip is coupled to the structure, such that wires of the first coil are contained within the crimps and do not lift the bottom surface of the strip from the structure;

applying a DC bias pulse to the first coil or the second coil;

applying an AC current to the coil not receiving the DC bias pulse;

wherein the DC bias current generator is further operable to apply the DC bias current during each AC pulse and for a period of time at least during both transmission of the guided wave and reception of the reflected signal and having a duty cycle of 10% or less.

14. The method of claim 13, wherein the sensor further has a padding layer placed along the length of the strip, at least between the crimps.

15. The method of claim 13, wherein the structure is tubular and the sensor has a circular geometry.

16. The method of claim 13, wherein the structure is planar and the sensor has a flat geometry.

17. The method of claim 13, wherein the steps of applying a DC bias pulse and applying an AC current are performed such that the DC bias pulse is turned on before the AC current pulse is turned on, and is turned off after the AC current pulse is turned off.

18. The method of claim 13, wherein the steps of applying a DC bias pulse and applying an AC current are performed such that the DC bias pulse is turned on before the AC current pulse is turned on, and is turned off after the acquisition of reflected guided wave signals is complete.

* * * * *